US00PP29254P3

(12) United States Plant Patent
Stemkens

(10) Patent No.: US PP29,254 P3
(45) Date of Patent: Apr. 24, 2018

(54) ***IBERIS* PLANT NAMED 'IBSZ0004'**

(50) Latin Name: *Iberis sempervirens*
Varietal Denomination: IBSZ0004

(71) Applicant: SYNGENTA PARTICIPATIONS AG, Basel (CH)

(72) Inventor: Henricus Godefridus Wilhelmus Stemkens, Andijk (NL)

(73) Assignee: Syngenta Participations AG, Basel (CH)

( * ) Notice: Subject to any disclaimer, the term of this patent is extended or adjusted under 35 U.S.C. 154(b) by 7 days.

(21) Appl. No.: 15/330,022

(22) Filed: Jul. 26, 2016

(65) Prior Publication Data

US 2016/0353637 P1 Dec. 1, 2016

Related U.S. Application Data

(60) Provisional application No. 62/252,746, filed on Nov. 9, 2015.

(30) Foreign Application Priority Data

May 28, 2015 (QZ) ..... PBR 2015/1116

(51) Int. Cl.
*A01H 5/02* (2018.01)

(52) U.S. Cl.
USPC ..... Plt./263.1

(58) Field of Classification Search
None
See application file for complete search history.

(56) References Cited

PUBLICATIONS

UPOV hit on *Iberis* plant named 'IBSZ0004', QZ PBR 20151116, filed May 28, 2015.*

* cited by examiner

*Primary Examiner* — Anne Marie Grunberg
(74) *Attorney, Agent, or Firm* — Dale Skalla

(57) ABSTRACT

A new *Iberis* plant named 'IBSZ0004' particularly distinguished by its cream white flowers that are early flowering, dark green foliage and a vigorous, mounded plant habit.

1 Drawing Sheet

Latin name of the genus and species of the plant claimed: *Iberis sempervirens*.

Varietal denomination: 'IBSZ0004'.

BACKGROUND OF THE NEW PLANT

The present invention comprises a new *Iberis*, botanically known as *Iberis sempervirens*, and hereinafter referred to by the variety name 'IBSZ0004'.

'IBSZ0004' is a product of a planned breeding program. The new cultivar 'IBSZ0004' has cream white flowers that are early flowering, dark green foliage and a vigorous, mounded plant habit.

'IBSZ0004' originates from a cross in a greenhouse in April 2007 in Enkhuizen, The Netherlands. The female parent was an unpatented, proprietary plant designated 'K0987-3' with small white flowers, lighter green foliage and is more branched when compared to 'IBSZ0004'.

The male parent of 'IBSZ0004' was an unpatented proprietary plant designated 'K1058-1', with larger white flowers and a more compact habit. The resultant seed was sown in August 2007 in Enkhuizen, The Netherlands.

'IBSZ0004' was selected as one flowering plant within the progeny of the stated cross in March 2008 in a greenhouse in Enkhuizen, The Netherlands.

The first act of asexual reproduction of 'IBSZ0004' was accomplished when vegetative cuttings were propagated from the initial selection in June 2008 in a greenhouse in Enkhuizen, The Netherlands.

BRIEF SUMMARY OF INVENTION

Horticultural examination of plants grown from cuttings of the plant initiated in June 2009 in Enkhuizen, The Netherlands, and continuing thereafter, has demonstrated that the combination of characteristics as herein disclosed for 'IBSZ0004' are firmly fixed and are retained through successive generations of asexual reproduction.

'IBSZ0004' has not been observed under all possible environmental conditions. The phenotype may vary significantly with variations in environment such as temperature, light intensity, and day length.

A Plant Breeder's Right for this cultivar was applied for in the European Union on May 28, 2015 and assigned No. 2015/1116. 'IBSZ0004' has not been made publicly available prior to the effective filing date of this application, notwithstanding any disclosure that may have been made less than one year prior to the effective filing date of this application by the inventor or another who obtained 'IBSZ0004' directly from the inventor.

The following traits have been repeatedly observed and are determined to be basic characteristics of the new variety. The combination of these characteristics distinguishes this *Iberis* as a new and distinct variety.

BRIEF DESCRIPTION OF THE PHOTOGRAPHS

The accompanying photographic drawings show typical flower and foliage characteristics of 'IBSZ0004' with colors being as true as possible with an illustration of this type.

Figure 1:
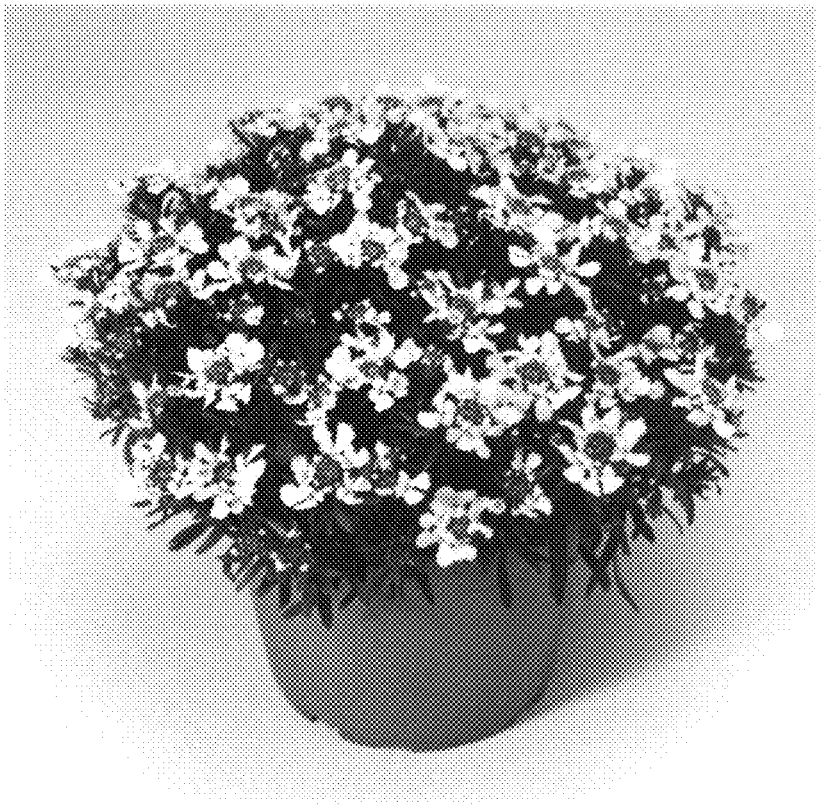
Figure 2:
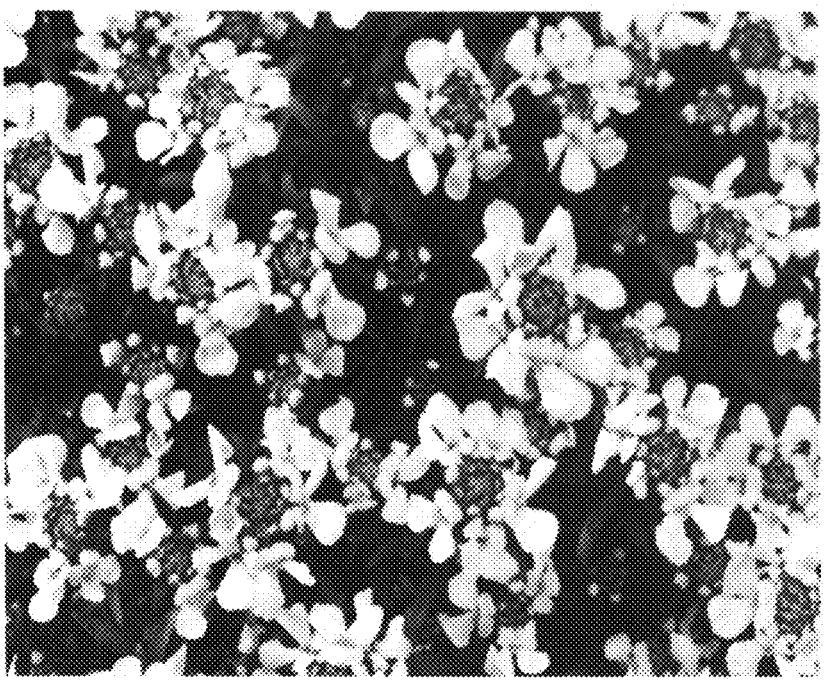

The photographic drawings show in FIG. 1 a flowering plant of the new variety and in FIG. 2 a close-up of the inflorescences.

DETAILED BOTANICAL DESCRIPTION

The plant descriptions and measurements were taken in Enkhuizen, The Netherlands under natural light in March 2015. These plants were approximately 34 weeks old and were growing in 13 cm pots in shade-house trials. The plants used for the photographs were about 34 weeks old growing in Enkhuizen, The Netherlands and the photographs were taken in March 2015.

Color chart used: Royal Horticultural Society Colour Chart (R.H.S.) 2001

TABLE 1

DIFFERENCES BETWEEN THE NEW VARIETY 'IBSZ0004' AND A SIMILAR VARIETY

| | 'IBSZ0004' | 'Snow Cone' (unpatented) |
|---|---|---|
| Flower size: | Smaller | Larger |
| Flower shape: | Bit Ruffled, denticulate | Smooth, entire |
| Branching habit: | More branching | Less branching |
| Peduncle color: | Light green | Dark green |

Plant:
- *Form, growth and habit.*—Dense, compact, mounded and branched.
- *Plant height.*—8.0-9.0 cm.
- *Plant height (inflorescence included).*—11.0-12.0 cm (without pot).
- *Plant width.*—28.0-30.0 cm.

Roots:
- *Number of days to initiate roots.*—About 9 days at about 18 degrees C.
- *Number of days to produce a rooted cutting.*—3 weeks at 18 degrees C.
- *Type.*—Fine, fibrous, white, well branched.
- *Color.*—RHS N155B but whiter.

Foliage:
- *Arrangement and attachment.*—Alternate simple-decussate, sessile.
- *Immature, leaf color, upper surface.*—RHS 135 A/B.
- *Lower surface.*—RHS 137A.
- *Mature, leaf color, upper surface.*—RHS 135B.
- *Lower surface.*—RHS 137A.
- *Length.*—0.8 (juvenile)-4.4 (adult) cm.
- *Width.*—0.15 (juvenile)-0.6 (adult) cm.
- *Shape.*—Linear.
- *Base shape.*—Attenuate, clasped to stem.
- *Apex shape.*—Acute.
- *Margin.*—Entire.
- *Texture, upper surface.*—Punctuate.
- *Lower surface.*—Punctuate.
- *Color of veins, upper surface.*—RHS 144C/N144C.
- *Color of veins, lower surface.*—RHS N144B.
- *Venation pattern.*—Pinnate.

Stem:
- *Quantity of main branches.*—About 12-15, with each a few lateral branches.
- *Color of stem.*—RHS 144B.
- *Length of stem.*—8.0-10.0 cm (including peduncle).
- *Diameter.*—0.2 cm.
- *Length of internodes.*—0.7-1 cm.
- *Texture.*—Punctuate, no hairs.

Inflorescence:
- *Type.*—Short simple corymb.
- *Quantity of inflorescences per plant.*—More than 150.
- *Inflorescence length.*—About 4.0 cm.
- *Inflorescence width.*—2.5-3.0 cm at widest point.
- *Lastingness of individual blooms on the plant.*—About 14 days.
- *Fragrance.*—None.

Bud (just before opening/showing color):
- *Color.*—Closest to RHS 142C.
- *Length.*—0.3 cm.
- *Width.*—0.35 cm.
- *Shape.*—Globose.
- *Pedicel color.*—RHS 144A.
- *Pedicel length.*—0.7-0.9 cm.
- *Pedicel diameter.*—0.7 cm.
- *Pedicel texture.*—Smooth to punctuate with pubescent to puberulous hairs.

Corolla:
- *Floret type.*—4 petals — 2 small and 2 large.
- *Floret diameter.*—1.0 cm.
- *Floret depth.*—0.65 cm.
- *Petal (all) color, upper surface.*—Closest to RHS N155D.
- *Lower surface.*—Closest to RHS N155D.
- *Upper/shorter petals.*—
- *Length.*—0.6 cm.
- *Width.*—0.4 cm.
- *Shape.*—Obovate to truncate.
- *Apex shape.*—Shallowly rounded.
- *Margin.*—Slightly retuse-denticulate.
- *Lower/longer petals.*—
- *Length.*—0.9 cm.
- *Width.*—0.7 cm.
- *Shape.*—Obovate to truncate.
- *Apex shape.*—Shallowly rounded.
- *Margin.*—Slightly retuse-denticulate.
- *Petal (all) texture, upper surface.*—Papillose.
- *Lower surface.*—Papillose.

Calyx:
- *Quantity.*—4 sepals.
- *Color, upper surface.*—RHS 143A/B.
- *Lower surface.*—RHS 143A/C.
- *Length.*—0.25 cm.
- *Width.*—0.1 cm.
- *Shape.*—Ovate-elliptic.
- *Apex shape.*—Acute.
- *Base.*—Fused.
- *Margins.*—Entire.
- *Texture, upper/inner surface.*—Lustrous.
- *Lower/outer surface.*—Lustrous.

Reproductive organs:
- *Gynoecium.*—
- *Pistil quantity.*—1.
- *Length.*—0.3-0.35 cm.
- *Style color.*—RHS 151C.
- *Style length.*—0.30-0.35 cm.
- *Stigma color.*—RHS 151A.
- *Stigma shape.*—Bi-lobed.
- *Ovary.*—Not very discernable.
- *Androecium.*—
- *Stamens, quantity.*—6; 4 longer, 2 shorter.
- *Color of filaments.*—Lighter than RHS 154C.

*Length of longer filaments.*—0.3 cm.

*Length of shorter filaments.*—0.15 cm.

*Anther color.*—RHS 7A.

*Anther length.*—0.05 cm.

*Anther shape.*—Oval.

*Color of pollen.*—RHS 13B.

*Pollen amount.*—Abundant.

*Fertility/seed set.*—Neither seed nor fruit production has been observed.

*Disease/pest resistance.*—Resistance to pathogens and pests common to *Iberis* has not been observed.

*Drought tolerance and cold tolerance.*—Hardy perennial. Tolerates high temperature to at least 30 degrees C. Tolerates low temperatures to minus 25 degrees C. No specific drought tolerance has not been observed.

What is claimed is:

1. A new and distinct variety of *Iberis* plant named 'IBSZ0004' substantially as illustrated and described herein.

* * * * *